(12) United States Patent
Madsen et al.

(10) Patent No.: US 7,618,391 B2
(45) Date of Patent: Nov. 17, 2009

(54) WAVEFORM SENSING AND REGULATING FLUID FLOW VALVE

(75) Inventors: Joseph R. Madsen, Newton, MA (US); Dentcho Ivanov, West Orange, NJ (US)

(73) Assignees: Children's Medical Center Corporation, Boston, MA (US); New Jersey Institute of Technology, Newark, NJ (US)

( * ) Notice: Subject to any disclaimer, the term of this patent is extended or adjusted under 35 U.S.C. 154(b) by 111 days.

(21) Appl. No.: 11/109,987

(22) Filed: Apr. 20, 2005

(65) Prior Publication Data

US 2006/0241545 A1      Oct. 26, 2006

(51) Int. Cl.
*A61M 5/00* (2006.01)
*H02N 2/00* (2006.01)
*H01L 41/00* (2006.01)
*F15B 13/04* (2006.01)
*F16K 31/02* (2006.01)

(52) U.S. Cl. .................... 604/9; 604/540; 310/317; 310/330; 310/345; 310/364; 137/596; 137/625.17; 137/325.33; 137/84; 251/129.02; 251/129.06

(58) Field of Classification Search .............. 310/317, 310/330, 345, 364; 604/9, 540; 137/596, 137/625.45, 625.17, 625.2, 625.33, 625.49, 137/625.5, 84, 85; 251/129.04, 129.06

See application file for complete search history.

(56) References Cited

U.S. PATENT DOCUMENTS

| | | | | |
|---|---|---|---|---|
| 3,769,531 A | * | 10/1973 | Elkuch | 310/309 |
| 4,492,360 A | * | 1/1985 | Lee et al. | 251/129.06 |
| 5,192,265 A | | 3/1993 | Drake et al. | |
| 5,322,258 A | * | 6/1994 | Bosch et al. | 251/65 |
| 5,354,032 A | * | 10/1994 | Sims et al. | 251/129.06 |
| 5,380,396 A | * | 1/1995 | Shikida et al. | 216/2 |
| 5,385,541 A | | 1/1995 | Kirsch et al. | |
| 5,387,188 A | | 2/1995 | Watson | |
| 5,405,316 A | | 4/1995 | Magram | |
| 5,529,465 A | * | 6/1996 | Zengerle et al. | 417/413.2 |
| 5,795,307 A | | 8/1998 | Krueger | |
| 5,901,939 A | * | 5/1999 | Cabuz et al. | 251/129.02 |
| 5,928,182 A | | 7/1999 | Kraus et al. | |
| 6,017,016 A | * | 1/2000 | Jackson | 251/129.06 |
| 6,068,751 A | * | 5/2000 | Neukermans | 204/601 |
| 6,095,175 A | * | 8/2000 | Miller et al. | 137/15.18 |
| 6,104,127 A | * | 8/2000 | Kameyama et al. | 310/346 |

(Continued)

OTHER PUBLICATIONS

Microchip PIC16F87/88 Data sheet, pp. 1, 113. Accessed Aug. 19, 2008. http://web.media.mit.edu/~jackylee/mas742/PIC16F88.pdf.*

(Continued)

*Primary Examiner*—Leslie R. Deak
*Assistant Examiner*—Adam Marcetich
(74) *Attorney, Agent, or Firm*—Thomas J. Engellenner; Nutter McClennen & Fish LLP

(57) ABSTRACT

Microfluidic shunt valves are disclosed having a deflectable element capable of being held in a closed position to occlude the passage of fluid between an inlet and outlet and, when not held in the closed position, the deflectable element is adapted to oscillate in response to fluid pressure pulses and thereby facilitate fluid passage through the valve. Controls for activating the deflectable element to permit fluid passage are also included.

33 Claims, 9 Drawing Sheets

U.S. PATENT DOCUMENTS

| | | | |
|---|---|---|---|
| 6,179,586 B1 * | 1/2001 | Herb et al. | 417/480 |
| 6,283,934 B1 | 9/2001 | Børgesen | |
| 6,348,042 B1 | 2/2002 | Warren, Jr. | |
| 6,383,160 B1 | 5/2002 | Madsen | |
| 6,408,878 B2 * | 6/2002 | Unger et al. | 137/597 |
| 6,431,212 B1 * | 8/2002 | Hayenga et al. | 137/855 |
| 6,581,899 B2 * | 6/2003 | Williams | 251/7 |
| 6,585,677 B2 | 7/2003 | Cowan, Jr. et al. | |
| 6,608,714 B2 * | 8/2003 | Hanson et al. | 359/296 |
| 2003/0234376 A1 * | 12/2003 | Cabuz et al. | 251/129.01 |

OTHER PUBLICATIONS

Koch, M; Evans, AGR; Brunnschweiler, A. "Simulation And Fabrication Of Micromachined Cantilever Valves." Sensors and Actuators, A, Physical, vA62, n1-3, pp. 756-759, 1997. ISSN: 0924-4247.*

Hyeun Joong Yoon, Ju Myoung Jung, Jin Suk Jeong, Sang Sik Yang. "Micro devices for a cerebrospinal fluid (CSF) shunt system." Sensors and Actuators A 110 (2004) 68.76.*

Alpern, et al., "Analysis of magnetic resonance imaging-based blood and cerebrospinal fluid flow measurements in patients with Chiari I malformation: a system approach," Neurosurg. Focus, vol. 11, pp. 1-10, Jul. 2001.

Chung, et al., "Development of MEMS-based Cerebrospinal fluid Shunt System," Biomedical Microdevices 5:4, 311-321, 2003.

Linninger, et al., "Hydrodynamics of the Human Brain," Laboratory for Product and Process Design, 2 pp.

Yoon, et al., "Micro devices for a cerebrospinal fluid (CSF) shunt system," Sensors and Activators A 110 (2004) 68-76.

* cited by examiner

— IMPEDANCE
---- PHASE

WAVEFORM SENSING AND REGULATING FLUID FLOW VALVE

BACKGROUND OF THE INVENTION

The present invention relates generally to the treatment of hydrocephalus, and more particularly relates to cerebrospinal fluid ("CSF") shunts.

Hydrocephalus is a condition in which cerebrospinal fluid accumulates in the ventricles of the brain. This accumulation of fluid increases the pressure within the ventricles and without medical intervention can cause brain damage and/or death to the patient. A common treatment for hydrocephalus is to use a fluid shunt system to drain excess CSF from the cerebral ventricles to a second body cavity, typically the peritoneal cavity. By draining the excess fluid, the elevated intracranial pressure is relieved. CSF shunts are well known and used broadly to treat patients with chronic hydrocephalus.

Generally, fluid shunt systems include a valve mechanism for controlling or regulating the flow rate of fluid through the system. Shunt systems typically permit fluid flow only when the fluid pressure reaches a threshold pressure that opens the shunt valve. Fluid flow normally continues until the intracranial pressure has been reduced to a level less than the threshold release pressure of the valve.

Thus, the flow regulating mechanism for most CSF shunts rely on pressure-sensitive valves that open when there is a sufficient pressure difference between the cerebral ventricle and the distal drainage cavity. In theory, this allows the right amount of the CSF to be drained. However, there are a number of problems associated with these shunts, for example, the control of the CSF flow typically is limited to a preset pressure. Although some shunt valves have mechanisms to adjust the pressure difference that triggers the valve to open, such mechanisms are typically cumbersome to use in real situations. In addition, the valves become clogged over time. Moreover, the existing shunts do not take into consideration the effects associated with CSF pulsations. The pressure in the cerebral ventricles will vary, typically in synchrony with the subject's heart rate. Under-drainage or over-drainage may arise due to the mismatched dynamic characteristics of the valve of the shunt and the CSF pulsations.

Accordingly, a need exists for a CSF shunt that can regulate the flow of CSF in a more controlled and intelligent manner. A need also exists for CSF shunts in which the dynamics are sensitive to the fluctuations and flow variation that arise due to CSF fluctuations.

SUMMARY OF THE INVENTION

Microfluidic shunt valves are disclosed having a deflectable element capable of being held in a closed position to occlude the passage of fluid between an inlet and outlet and, when not held in the closed position, the deflectable element is adapted to oscillate in response to fluid pressure pulses and thereby facilitate fluid passage through the valve. Controls for activating the deflectable element to permit fluid passage are also included.

Microfluidic shunt valve arrays are also disclosed with a plurality of valves that control cerebrospinal fluid flow depending on the CSF pulse rate. A subset of the plurality of valves can be kept in reserve so that if, during operation, a valve becomes clogged, the system automatically reacts by replacing the failing valve with another one from the valve reserve. The array of valves can also include valves with different characteristics, such as size and/or resonant frequency, to optimize fluid flow control under various conditions. An impedance sensor can detect the impedance changes caused by valve clogging or less than desired valve performance and provide a signal to controller, which brings a new valve (or valves) from the reserve into play.

Each valve can contain an oscillating valve element capable of moving in resonance with the CSF pulsations. The operation of each valve can be modulated by AC and DC capacitance forces provided by AC and DC voltages between the oscillating valve element and other conductive layers in a sandwich-like, integrated circuit structure. The DC component can provide a bias voltage controlling the oscillating valve element's oscillation amplitude and the opening of the valve. The AC component can induce the oscillating valve element to oscillate in phase and/or synchrony with the CSF pulsations. Ideally, the AC signals and the CSF flow pulsations have the same frequency.

The oscillating valve elements of the present invention are able to provide a fast response to variations in the CSF flow dynamic parameters. An impedance sensor monitors the impedance values of all oscillating valve element's and provides feedback signals to the controller. Impedance changes caused by valve clogging or perturbations in the CSF pulsations are monitored, and a feedback signal from the impedance controller to the processor triggers a corrective response.

Accordingly, in one aspect, the invention features a microfluidic shunt valve formed as part of a semiconductor chip having at least one inlet and at least one outlet for fluid passage therebetween. The terms "semiconductor chip" and "chip," as used herein, is intended to encompass devices fabricated at least in part from a substrate material, e.g., a silicon or silicon-on-insulator (SOI) wafer. Typically two or more valve elements are formed on (or in) such a substrate material by lithographic patterning, etching and similar processes well known to those skilled in the art. In addition, the "chip" need not be monolithic but may consist of a plurality of segments or layers that bonded together or otherwise coupled. All of the components of a "chip" do not need to be electrically conductive (or insulating), but can also include structural or otherwise ancillary elements as well. Illustrative examples are described in more detail below.

The valve may further comprises at least a first electrode and a second electrode, the first electrode associated with the deflectable element and isolated from the second electrode such a voltage applied between the first and second electrodes can induce movement of the deflectable element. The valve can also be structured such that movement of the deflectable element can cause occlusion of the inlet or outlet.

A current regulator can be used for applying voltage between the first and second electrodes to bias the deflectable element in one position or to dampen oscillation. The current regulator can also be used for applying an alternating current to at least one of the electrodes. The current regulator can further be adapted to adjust at least one of DC voltage, or alternating current amplitude, frequency or phase in response to a control signal. The valve can also further comprise at least one impedance sensor for monitoring oscillations of the deflectable member.

In another aspect, the invention provides for an array of valves, each valve being substantially as described above, and a controller. Accordingly, the invention further encompasses microfluidic valve assemblies with a plurality of valves, each valve comprising a channel to guide flow of a fluid and a deflectable valve element disposed within the channel. The deflectable valve elements are capable, when activated, of oscillating in response to fluid pulses to permit fluid passage. The assembly further comprising electrical controls for activating a subset of the plurality of valves, and at least one impedance sensor for monitoring movement of the deflectable member.

In this aspect, the present invention differs from conventional shunt valves which rely, for the most part, on a threshold pressure differential to open (and in some instances an maximum pressure differential for operation to prevent over drainage due to siphoning effects). In contrast to these static designs, the shunt valves and valve arrays of the present invention permit more precise control over the fluid transport. By controlling the number of valves operational at any given time and/or the oscillation of their deflectable gate elements, the volume and rate of fluid transport can be readily controlled without resort to fixed threshold or maximum pressure parameters. Thus, the present invention permits essentially pressure independent control of cerebrospinal fluid transport, limited only by CSF pulsation and the elastic modulus of the deflectable gate.

In a further aspect, the invention features a microfluidic shunt valve comprising a micro-machined structure defining a channel to guide flow of a fluid therethrough in a primary direction. A deflectable valve element can be disposed within the channel, and is capable of oscillating in response to fluid pulses to permit fluid passage. In this shunt valve, the deflectable valve element is electrically isolated from at least a portion of the structure to permit impedance measurements of an oscillatory frequency of the deflectable valve element.

The deflectable valve element can be electrically biased in a normally closed valve position, and a sensor can be used for measuring changes in impedance. In addition, a controller can be used for modulating the oscillatory frequency. The controller can include a regulator adapted to apply a current that alternates at a desired frequency. The regulator can also be adapted to apply a direct current bias.

In yet another embodiment, the invention features a shunt valve including a valve body with a distal end and a proximal end. A valve assembly can be disposed upon a semiconductor chip, the valve assembly having a plurality of deflectable valve elements, where each valve element is capable of oscillating in response to fluid pulses, and where each valve element is electrically isolated from at least a portion of the chip to permit impedance measurements of an oscillatory frequency of the valve element.

The array assembly can further comprise a sensor for measuring changes in impedance of at least one valve element, and a controller for modulating the oscillatory frequency. The controller can include a voltage applicator adapted to apply an alternating current that is, preferably, adjustable to a desired frequency and the voltage applicator can further be adapted to also apply a direct current bias to deactivate particular valves (or dampen their movements).

In yet another aspect, the invention features a method of treating hydrocephalus in a subject by implanting a shunt with a distal end and a proximal end in the subject, where the proximal end is implanted in a brain ventricle and the distal end is implanted in a region other than the brain. The shunt comprises a valve assembly having a plurality of channels to guide flow of cerebral spinal fluid (CSF), with each channel having a deflectable valve element disposed therein, which is capable, when activated, of oscillating in response to fluid pulses to permit fluid passage. At least one of the valve elements is activated and the operation of the activated valve element is monitored. If necessary, at least one additional valve element is activated based on the monitored valve operation.

Each valve element can further comprise at least a first electrode and a second electrode, the first electrode associated with the deflectable element and isolated from the second electrode, the method further comprising applying an alternating voltage between the first and second electrodes to induce movement of the deflectable element. The applied voltage can maintain a subset of the valve elements in a closed position.

The method can further comprise applying an alternating current to the first electrode to facilitate oscillation of the deflectable element, or to facilitate impedance measurements. Moreover, at least some of the deflectable elements can have different resonant frequencies and the method can further comprise selecting at least one deflectable element with a desired resonant frequency based on one or more impedance measurements.

The valve assembly can have a plurality of deflectable valve elements in subsets of a different size. The deflectable valve elements can be activated upon occlusion of another subset of deflectable valve elements, or activated upon a change in pulse rate of the CSF.

In yet another aspect, the invention features a method of fabricating a micro-electro-mechanical-system (MEMS) valve assembly. The method comprises providing a SIMOX wafer having a first silicon layer, a second silicon layer and a buried oxide disposed therebetween. A plurality of channels can be formed in the first silicon layer, and a plurality of gate structures can be formed in the second silicon layer, each gate structure being aligned with a channel of the first layer. A portion of the oxide layer between the gate structures of the first layer and the second layer can be removed to permit deflection of the gate structures. Electrical leads to each gate structure are also provided, such that a voltage applied between a gate structure and the first layer can induce deflection.

The method can further comprise p-doping the first layer, and n-doping the second layer. Other doping schemes, such as the use of p-doped and p+-doped layers, will be apparent to those skilled in the art. The step of forming the channels can further comprise patterning a resist and then etching the channels in portions of the first layer not protected by the resist.

The step of forming the gate structures can further comprise patterning a resist and then etching the gate structures in portions of the second layer not protected by the resist. The method can further include the step of depositing an conductive material to form an electrode on each gate structure, or depositing a conductive material to form an electrode on at least a portion of one or more of the layers.

BRIEF DESCRIPTION OF DRAWINGS

A more complete understanding of the invention may be attained by reference to the drawings, in which like reference numerals indicate the same or equivalent element.

DETAILED DESCRIPTION

Figure 1:
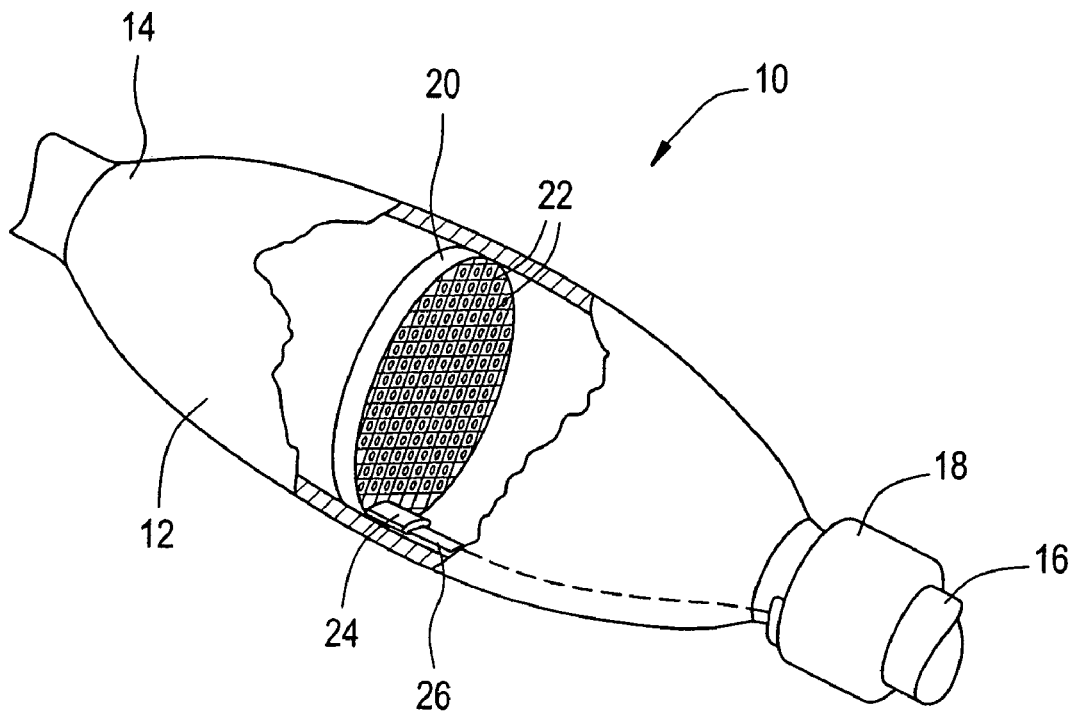
FIG. 1 is a schematic partially cut, perspective view of a shunt valve of the invention.

FIG. 1 is a schematic view of a shunt valve 10 having a valve body 12, a proximal end 14, a distal end 16, and a power supply and electronic controls 18. The shunt valve comprises a valve assembly 20 with a plurality of deflectable valve elements 22, a connector 24, and associated electrical conduits 26 that serve to couple the valve assembly 20 with the power supply and electrical controls 18. The term "deflectable" and variants thereof as used in this specification is intended to include bending, shifting, swinging, stretching and elastic deformation as well as other forms of physical movement.

Figure 2:
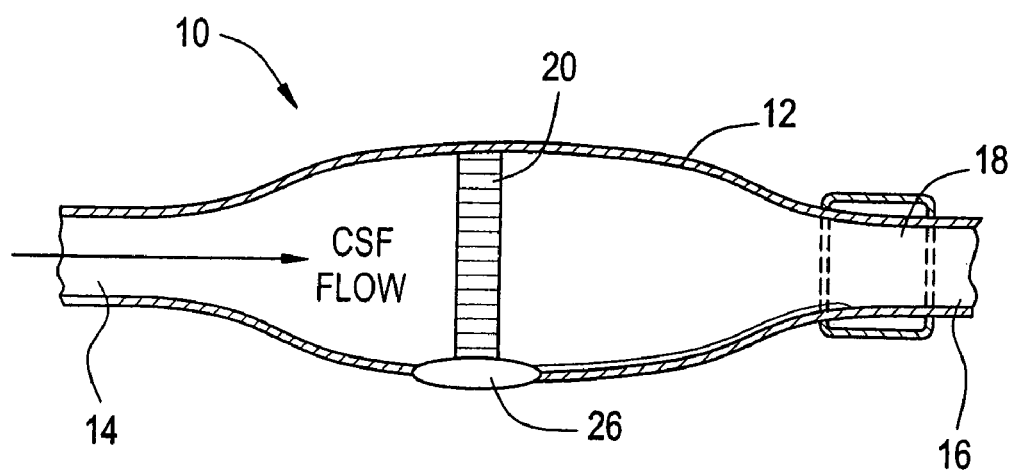
FIG. 2 is a schematic sectional view of the shunt valve of FIG. 1.

FIG. 2 a schematic sectional view of the shunt valve. The valve body 12 houses the shunt valve assembly 20 which has a plurality of deflectable valve elements 22. The shunt valve assembly 20 is designed to facilitate the passage of cerebrospinal fluid (CSF) from the proximal end 14 to the distal end 16 when the pressure differential between the ventricle and the distal cavity is greater than a threshold value. More importantly, the valve of the invention allows "fine" control of CSF by operating deflectable valve elements at the same oscillation frequency as the CSF pulsation. This provides a valve with dynamics that are sensitive and which are optimized for CSF pulsation in each individual patient.

Figure 3:
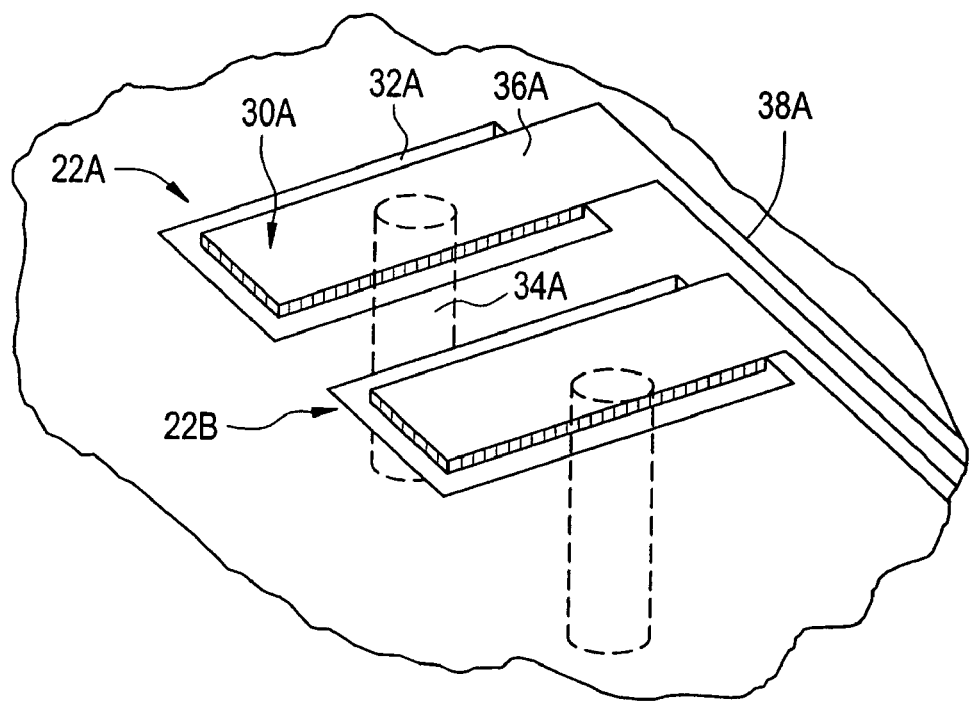
FIG. 3 is a schematic perspective view of a portion of the shunt valve of FIG. 2 showing individual valve elements.

FIG. 3 is a schematic perspective view of the shunt valve showing two individual valve elements 22A and 22B disposed within the valve assembly 20. Each valve element 22A has a gate element 30, and a chamber 32 having an outlet hole 34 (shown in phantom). The gate element 30 comprises an electrically conductive upper surface 36A and an electrical lead 38. The valve element 22B has comparable structures to element 22A. A plurality of valve elements provide the valve assembly 20.

Figure 4A:
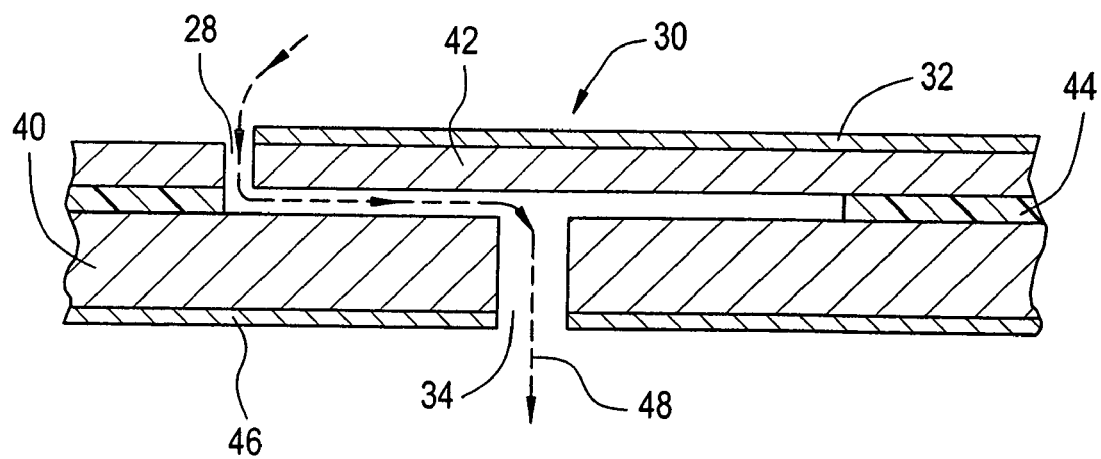
FIG. 4A is a schematic cross-sectional view of an individual valve element in an open position.
Figure 4B:
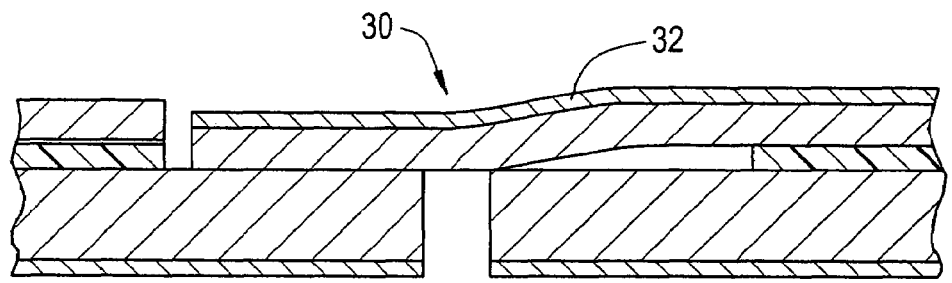
FIG. 4B is a schematic cross-sectional view of the individual valve element of FIG. 4A in the closed position.

FIG. 4A is a more detailed cross-sectional view of a single valve element 22 in an "open" position. The valve element comprises a silicon substrate 40 and a silicon surface layer 42 separated by an oxide layer 44. The silicon surface layer 42 acts as a cantilever that is sufficiently flexible such that it can respond to naturally occurring CSF pulsation pressure. The deflectable valve element further includes a lower electrode 46. The "open" position permits the CSF 48 to enter the inlet 28 and exit through the outlet 34. FIG. 4B shows a schematic perspective view of an individual valve element 22 in a "closed" position. In the closed position, the CSF flow is occluded by the silicon surface layer 42 contacting the silicon substrate 40. The term "occlude" and variants thereof to include both stopping and substantially inhibiting passage of fluid.

The design facilitates the manufacture of array elements using micro-electro-mechanical systems (MEMS) technology and a "silicon-on insulator" ("SOI") or "separated-by-insulating-metal-oxide (SIMOX) wafers as a starting material. The manufacturing technique is described in detail below. The term "MEMS" as used herein is not intended to denote a strict size category of devices. MEMS devices can be as large as several millimeters or as small as 10 nanometers, depending upon the techniques used and the desired applications.

Figure 5:
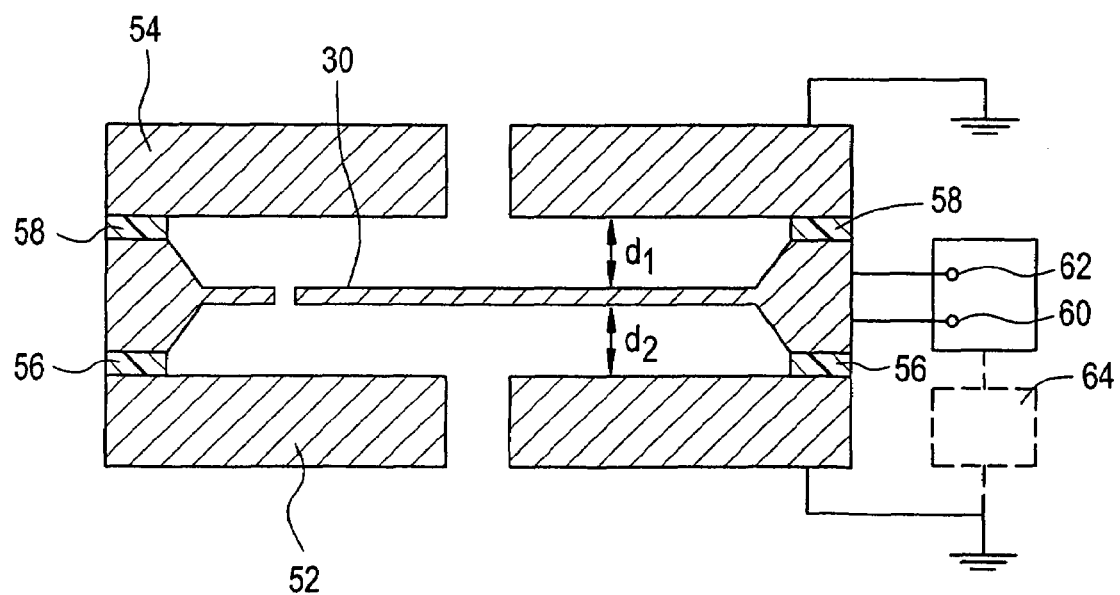
FIG. 5 is a schematic cross-sectional view of an alternative embodiment of a valve element.

FIG. 5 is an alternative embodiment of the valve element 50 with an electrically conductive gate element 30 (e.g., an oscillating central cantilever) is situated between a lower silicon block 52 and an upper silicon block 54, separated by oxide layers 56 and 58. Both upper and lower silicon blocks 52 and 54, respectively, are electrically conductive and preferably grounded. The design facilitates oscillations of the gate element 30 in response to pulsation of the CSF. The design also facilitates measurement of impedance. The electrically conductive gate element 30 can be biased with a DC voltage by electrode 60. Additionally, and alternating current (AC) can be applied by electrode 62. As discussed in more detail below, an impedance sensor 64 can also be deployed to provide feedback signals. The sensor can monitor the valve performance by measuring impedance changes over time.

It will be appreciated that the terms "upper" and "lower" are used simply for illustrative purposes and do not correspond to any particular orientation. The valves of the present invention are not limited to vertical operation. For a device implanted in a patient, the orientation may change as the orientation of the patient changes.

As shown in FIG. 5, the valve is divided into an upper chamber 51 and a lower chamber 53. Fluid flows from the upper chamber to the lower chamber whenever the gate 30 is allowed to swing. In one embodiment the depth of each chamber can range from about 10 to 500 micrometers, more preferably from about 25 to 100 micrometers. The width of each chamber can range from about 50 to about 1000 micrometers, more preferably from about 50 to about 250 micrometers. The dimensions of chambers 51 and 53 can be the same or different. As shown in FIG. 5, the upper chamber 51 is smaller than lower chamber 53, which can be advantageous to increase fluid transport (from the upper to the lower chamber as illustrated). On the other hand, a reduction in the size or depth of the lower chamber can be advantageous to provide an anti-siphon effect when an ambulatory patient changes orientation.

In operation, the threshold pressure for opening the valve can be controlled by electrostatic force, e.g. by applying a DC bias voltage to the central cantilever layer while maintaining upper and lower silicon blocks at relative ground, as shown in FIG. 5. As the voltage difference is increased, the threshold necessary for valve opening will likewise increase. A high DC bias can also be employed to maintain certain valves closed, e.g., to hold a number of valve elements in reserve. Moreover, in the case of an array having different subsets of valves, in which one or more subsets are designed for particular conditions, the DC bias voltage can be used to activate only the optimal subset for a particular condition.

Once the valve is opened, an AC current can also be imposed to help "tune" the oscillations of the cantilever and maintain synchrony with the frequency of CSF pulses. The AC current can also provide additional energy to the oscillating lever cantilever to accommodate changes in the CSF pulse frequency or compensate for fluid resistance effects.

Figure 6A:
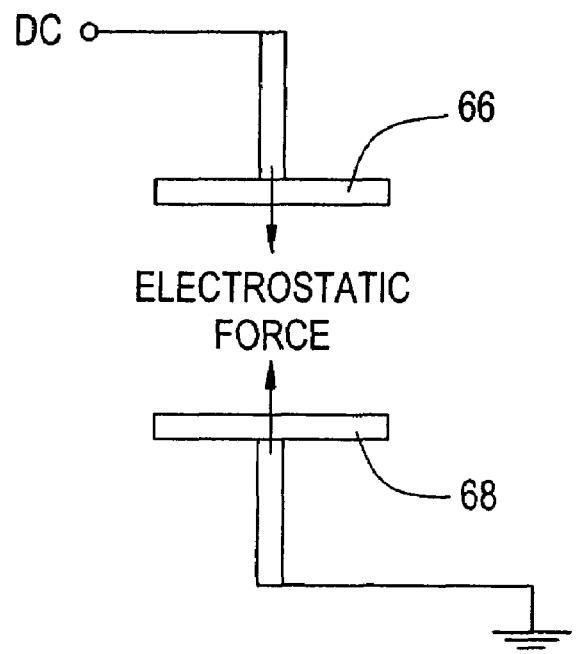
FIG. 6A is a schematic illustration of electrostatic forces utilized in the present invention.
Figure 6B:
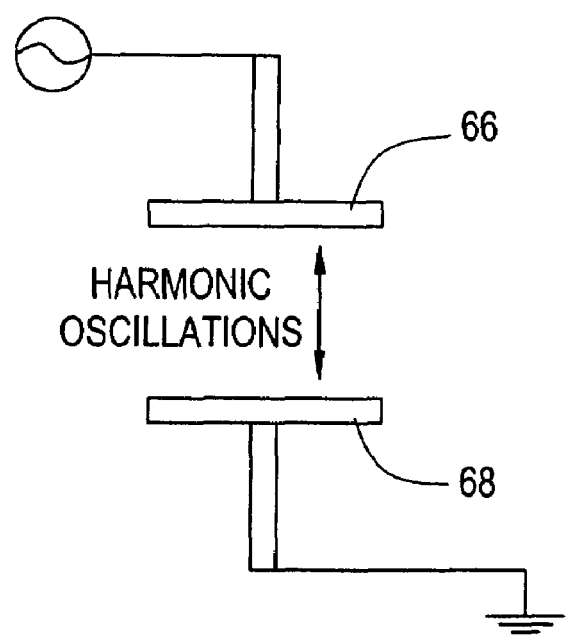
FIG. 6B is a schematic illustration of harmonic oscillations utilized in the present invention.

FIG. 6A illustrates one mechanism of operation of the present invention. When a DC voltage is applied between an upper plate 66 and a lower plate 68, electrostatic forces will cause the plates to be attracted to each other. This principle is used in the invention to close the valve as shown in FIG. 4B. Where the electrostatic forces draw closer to the silicon substrate, contact is established, thereby closing the outlet 28. FIG. 6B shows that additional AC current is used on the plates 66 and 68 to induce harmonic oscillations which correlate with the CSF pulse rate.

The natural oscillation of a beam or cantilever at its resonant frequency can be defined in part by its quality factor, also known as its "Q factor," which is a measure of energy loss when a oscillating element experiences energy losses due to friction and the like. A high Q system will maintain it amplitude with minimum intervention while a low Q system is termed "damped." In the present invention, the effect of a surrounding fluid will inherently have a damping effect of oscillations of the deflectable gate element 30, as shown in the figures. Impedance measures can be used to monitor such losses and, if necessary, provide a compensatory "boost" or other remedial action.

Impedance measures the degree to which an electric circuit resists electric-current flow when a voltage is impressed across its terminals. Impedance, expressed in Ohms, is the ratio of the voltage impressed across a pair of terminals to the current flow between those terminals. In direct-current (DC) circuits, impedance corresponds to resistance. In alternating current (AC) circuits, impedance is a function of resistance, inductance, and capacitance. Inductors and capacitors build up voltages that oppose the flow of current. This opposition, called reactance, must be combined with resistance to determine the overall impedance. The reactance produced by inductance is proportional to the frequency of the alternating current, whereas the reactance produced by capacitance is inversely proportional to the frequency.

Figure 6C:
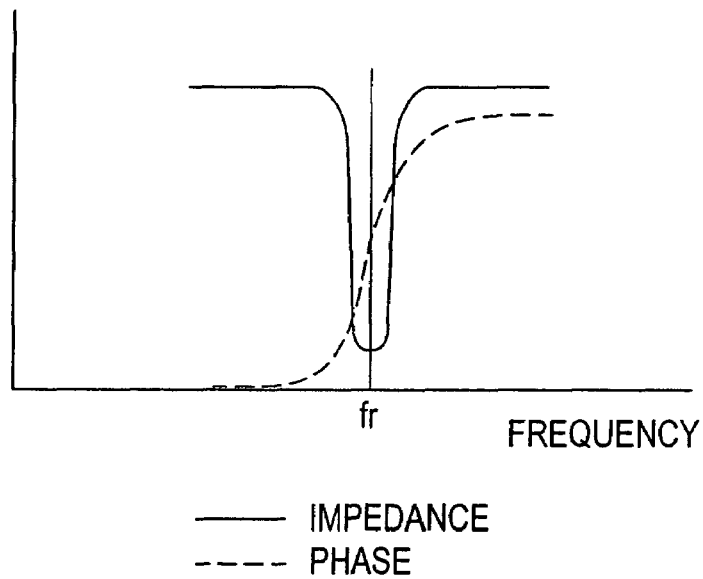
FIG. 6C is an illustrative graph of phase and impedance versus frequency for an oscillating gate element (in arbitrary units)

FIG. 6C is an illustrative graph of phase and impedance versus frequency for an oscillating gate element (in arbitrary units). In a damped system, such shown in FIG. 5, the actual phase of oscillations will trail the natural resonant frequency, f, by a factor, Δf, which can be detected as an impedance. The phase of the driving AC voltage can be adjusted (advanced) to balance out frictional losses. Thus, continued monitoring of the impedance and feedback control adjustments can be used to maintain synchrony as well as to adapt to new conditions, e.g., changes in heart rate or patient activity levels, or simply to "fine-tune" valve operations.

In the present invention, a controller can monitor the impedance (or phase) of the AC signals transmitted through each valve. At resonance the impedance will exhibit a minimum value (i.e. the resistivity exhibits its minimum value and, conversely, conductivity exhbits its maximum value). The relationship between impedance and phase is shown in the FIG. 6C. At resonance, the impedance exhibits a minimum value while the phase curve, which has been going up with frequency, exhibits a sign change (inversion) of the slope. In operation, for example, if a valve is blocked by debris, both impedance and phase curves will disappear and the valve will start to behave like a heavily damped resonator. The Q factor of a stuck valve will approach zero, the impedance curve will broaden (large delta f), and the phase curve will flatten. Since the controller is monitoring all valves, if a high impedance value and no phase change for a certain valve is detected, the controller automatically can switch valves, putting another valve with normal resonant characteristics to work.

Figure 7:
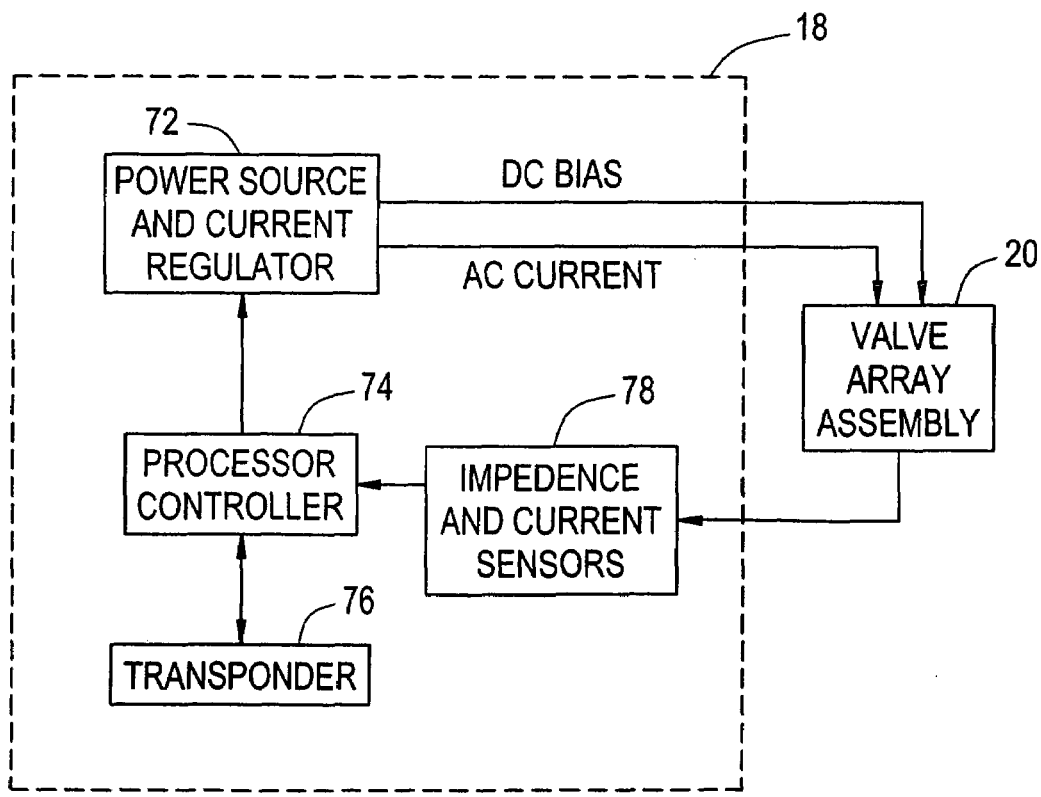
FIG. 7 is a block diagram of a waveform sensing valve system according to the invention.

FIG. 7 is a block diagram of a feedback control system, showing a power source and current regulator 72, connected to a processor 74 such as a digital signal processor (DSP), which sends and receives signals from a transponder 76. An impedance current sensor 78 receives signals from the valve array 20 and communicates these signals to the processor 74. All elements 72-78 can be incorporated into a single body power supply and electrical control system 18, as shown in FIG. 1.

The DSP controls the operations of all valves in the shunt array through the AC/DC voltage source and an impedance controller. The DSP receives feedback signals from the impedance controller. If a change in the CSF pulsation characteristics occurs the controller detects the resulting impedance changes and sends an alarm signal to the DSP. The DSP makes the necessary corrections in frequency, phase, flow, and number of valves participating in the process at a given moment of time through the AC and DC voltage sources. Valve clogging results in changes in the resonant-cantilever's impedance. The impedance controller detects the failing valve and submits an alarm signal to the DSP. The DSP automatically responds by replacing the failing valve with another one from the reserve valves. The DSP can bring to operation various numbers of valves at various times depending on the CSF characteristics and the feedback signals from the impedance controller. This ensures accurate monitoring of the CSF flow and avoids over-draining or under-draining of CSF from the ventricles. Over-draining or under-draining CSF occurs because of mismatched dynamic characteristics of the valves and the CSF pulsations.

Most generally, the invention encompasses microfluidic valve arrays in which fluid conditions, such as pulse frequency and amplitude (e.g., pressure), are detected and monitored as electronic waveforms and such waveforms are used to select particular subsets of valves or modulate the behavior of one or more valve elements.

Figure 8A:
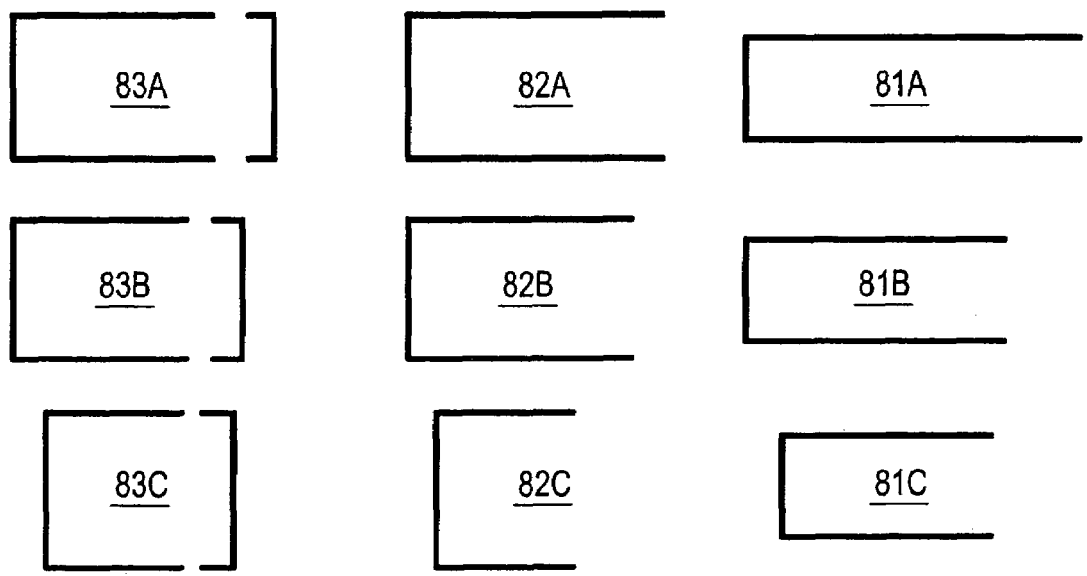
FIG. 8A is a top view of the valve elements that can be utilized in the invention.
Figure 8B:
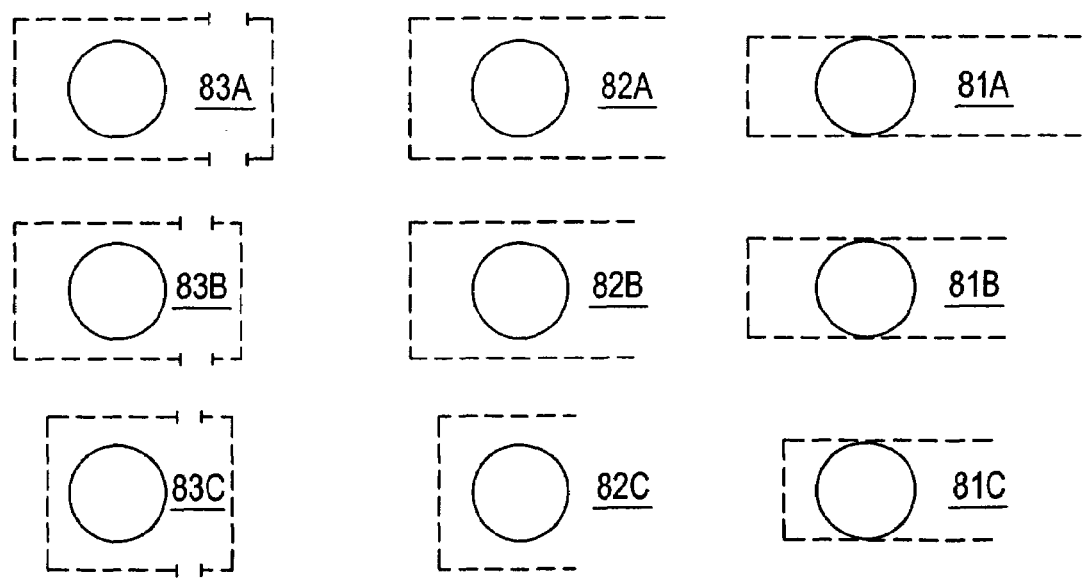
FIG. 8B is the bottom view of valve elements of FIG. 8A.

FIGS. 8A and 8B are top and bottom views, respectively of an illustrative valve array having individual valve elements with different shapes and sizes. Each subset of valves operates at an optimal resonant frequency. The geometry of each gate element responds best to the particular resonant frequency based of the pulsation of CSF and the measured impedance. If the patient is likely to have variations in CSF pulse rate, the invention permits electronic monitoring and activation of particular subsets of valves whose resonant frequency is best tuned to the pulse rate of the CSF. For example, valves 81A, 81B and 81C illustrate gate designs of different length, each of which will exhibit a optimal resonant frequency. Further fine-tuning of the resonant frequency can be achieved by also varying the width of the gate, as illustrated by valve elements 82A-C. Valves 83A-C illustrate an alternative gate design in which the cantilever gate element is replaced by one that creates a fulcrum-like effect. In operation, each of the illustrated valves will respond differently to a particular pulse frequency of the CSF. Impedance measures permit real-time feedback control of the valve array and selection of particular valves best suited to the patient's conditions.

Figure 9A:
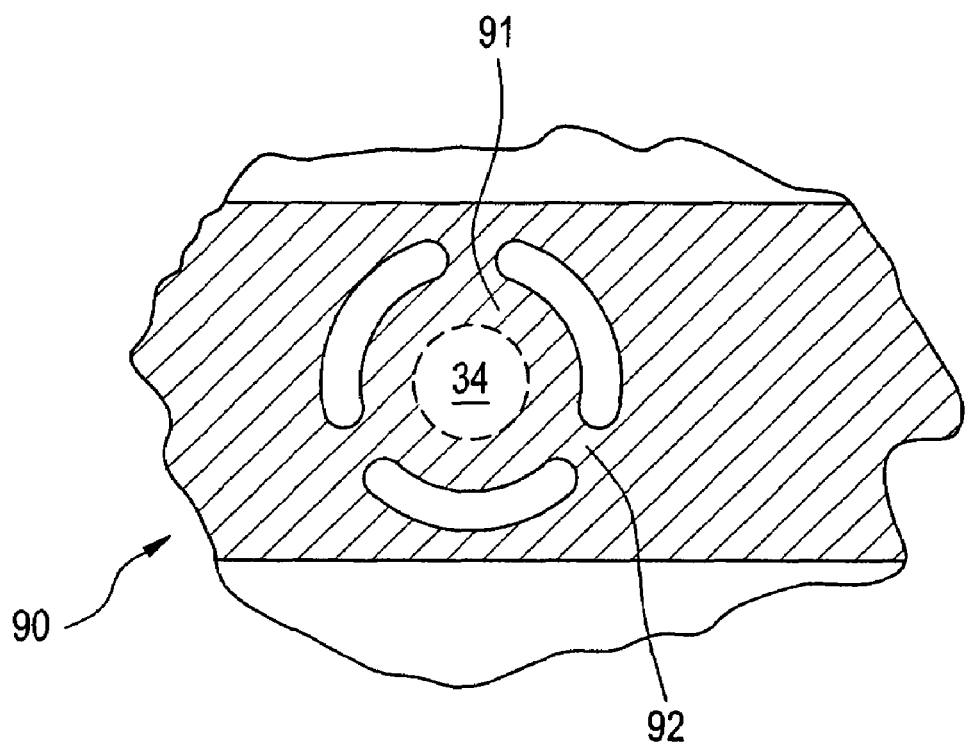
FIG. 9A is a top view of an alternative embodiment of a valve element.
Figure 9B:
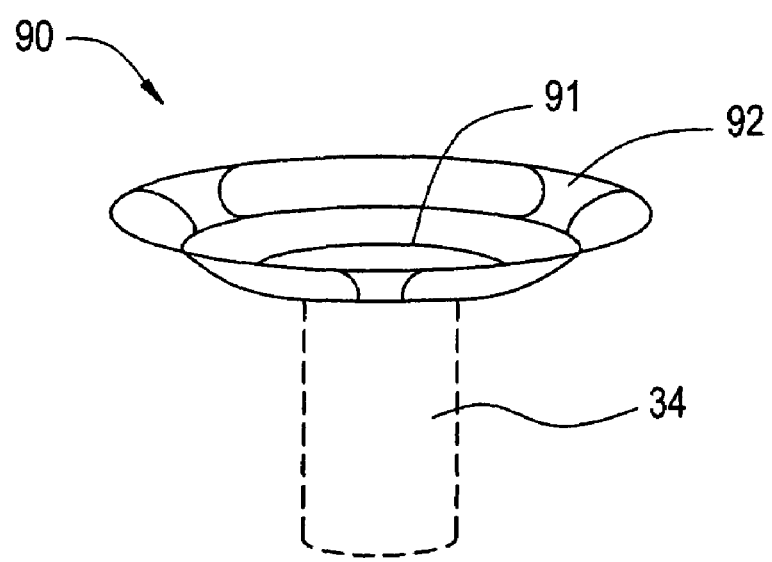
FIG. 9B is a schematic perspective view of the a valve element of FIG. 9A.

FIG. 9A is a top view of another embodiment of a valve 90 of the invention showing a gate element 91 and an outlet port 34. FIG. 9B shows a side view of the valve showing the gate element 91 coupled to the silicon substrate with finger elements 92 which permit deformation in response to applied voltages. This permits the outlet 34 to "open" and "close" in resonance with the pulse rate. Again, the illustrated valve 90 can be part of an array of valves having different resonant characteristics, e.g., formed by varying the size of the gate 91 and/or the properties of the finger elements 92.

FIGS. 10A-E provide an illustrative set of manufacturing steps for creating a valve of the invention using wet chemical etch, deep reactive ion etching (DRIE), photolithography, and thin film deposition techniques. The first step, shown in FIG. 10A, begins with a silicon-on-insulator (SOI) type wafer 100, e.g., a SIMOX wafer, having a buried silicon oxide layer 102 disposed between an upper silicon layer 101 and lower silicon layer 103. The upper silicon layer can be an n-type doped silicon region while the lower silicon layer can be a p-type silicon region. The thickness of the SOI silicon film can be, for example, in the range of about 10 microns to 25 microns.

Figure 10A:
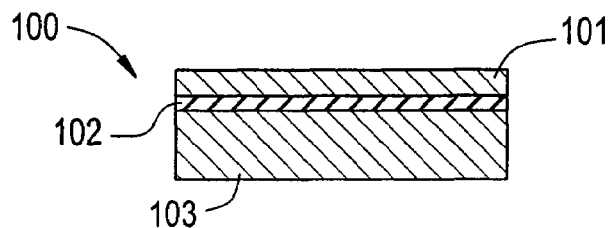
FIG. 10A is an illustration of the initial step in forming the valve of FIG. 4A.
Figure 10B:
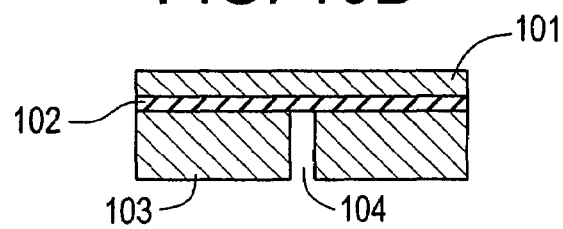
FIG. 10B is an illustration of the second step in forming the valve of FIG. 4A.
Figure 10C:
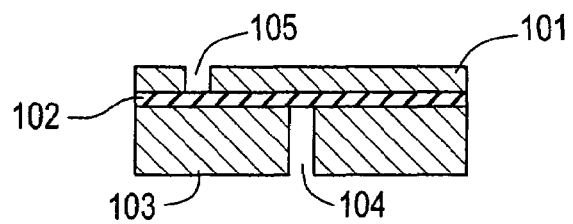
FIG. 10C is an illustration of the third step in forming the valve of FIG. 4A.
Figure 10D:
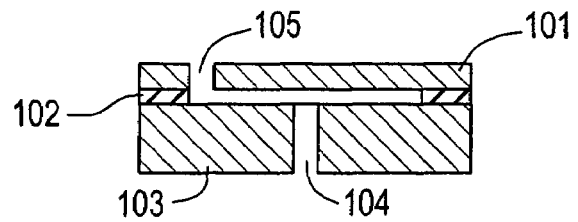
FIG. 10D is an illustration of the fourth step in forming the valve of FIG. 4A.
Figure 10E:
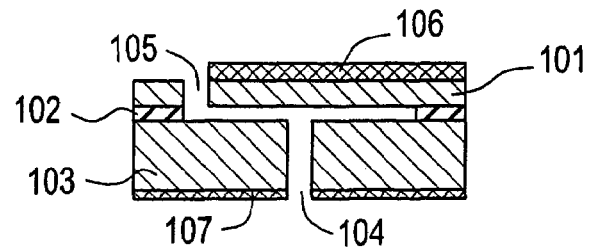
FIG. 10E is an illustration of the fifth step in forming the valve of FIG. 4A.

In FIG. 10B a microfluidic input channel 104 is etched into the p-type doped lower silicon layer 103 using, for example, deep reactive plasma etching. In the next step, shown in FIG. 10C, a portion 105 of the upper n-doped silicon layer is removed by etching (See FIG. 8A also). The next step shown in FIG. 10D involves removing a portion of the oxide layer 102 between the upper and lower layers to form a resonant cantilever. The final step, shown in FIG. 10E, involves depositing a electrodes 106 and 107 (e.g., gold electrodes) on the upper and lower doped silicon wafers using techniques such as a gold etch bath. One or both of the electrodes can be grounded. It should be apparent that various intermediate steps such as resist deposition and patterning have been omitted from the foregoing schematic illustrations. Such steps are well known to those skilled in the art.

A plurality of these valves can be created to produce a valve array that can be housed in a valve body. The valve of the invention replaces the functions of conventional shunts and provides better control of the CSF flow from the ventricles to the distal location than conventional shunts. The valve arrays of the invention has a high-accuracy control over the CSF flow, fast response to various changes in the CSF flow dynamics, and the capability to operate synchronously with the CSF pulsations.

Figure 11A:
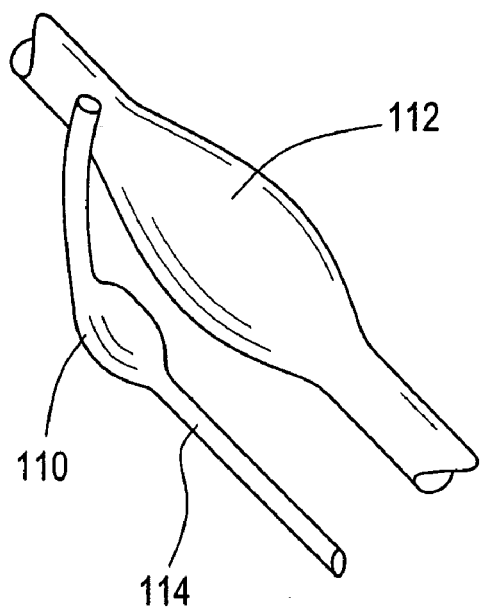
FIG. 11A is a schematic perspective view of a tandem valve assembly employing a microfluidic valve array and a conventional pressure-sensitive valve.
Figure 11B:
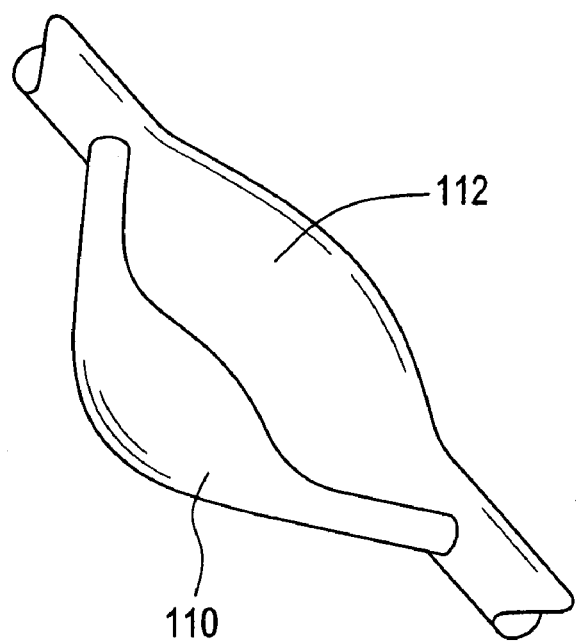
FIG. 11B is a schematic perspective view of another embodiment of a tandem valve assembly employing a microfluidic valve array and a conventional pressure-sensitive valve.

The present invention can also be used in tandem with a conventional pressure-sensitive shunt valve device to provide an emergency safety feature, in the event the primary valve becomes fouled or is otherwise rendered inoperative. Two such tandem configurations are shown in FIG. 11A and FIG. 11B. In FIG. 11A, a microfluidic valve array 110 is illustrated as a alternative path which can be activated in the event that a conventional shunt valve 112 becomes clogged or otherwise malfunctions. As shown in FIG. 11A, the microfluidic valve array 110 has its own drainage catheter 114 that provides an independent drainage pathway. In FIG. 11B, the microfluidic valve array 110 is shown in a tandem configuration to permit CSF to by-pass the conventional shunt valve 112. The tandem configuration of FIG. 11B utilizes a single drainage catheter but permits the microfluidic valve array to assist the main valve 112.

Although the present invention has been described herein primarily in connection with CSF shunt systems, the structures, systems and methods are equally applicable to other biomedical fluid control problems. For example, the microfluidic valves can also be used to control urine, blood or endocrine fluid transport and/or employed in catheters, hemodialysis, drug infusion, tissue engineering and other applications as well as in artificial organs or organ assist devices, e.g., in kidney, liver, bladder and heart replacement or assist devices.

It is understood that the geometry, dimensions, and materials can vary depending upon the requirements of particular applications and the anatomy of the patient. The housing can be constructed from suitable non-toxic and bioimplantable materials, such as medical grade silicones, polyurethanes, or other polymeric materials. In one embodiment, the housing can be constructed of an injection molded plastic. Although the housing is primarily shown and described as having a rectangular shape, it is understood that other geometries are possible such as cylindrical and polygonal structures.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A microfluidic shunt valve for controlling the flow of pulsed fluid comprising
   a chip having at least one inlet and at least one outlet for fluid passage therebetween;
   an oscillating valve element having a deflectable element capable of being held in a closed position to occlude the passage of fluid between the inlet and outlet and, when not held in a closed position, further configured to oscillate in response to fluid pressure pulses and thereby facilitate fluid passage through the valve; and
   controls for activating the oscillating valve element to permit fluid passage.

2. The valve of claim 1, wherein the valve is further structured such that movement of the deflectable element can cause occlusion of the inlet or outlet and the valve further comprises at least a first electrode and a second electrode, the first electrode associated with the deflectable element and isolated from the second electrode such a voltage applied between the first and second electrodes can induce movement of the deflectable element to close the valve.

3. The valve of claim 2, wherein the first and second electrodes are configured to permit impedance measurements of oscillatory movements of the deflectable element.

4. The valve of claim 2, wherein the valve further comprises a current regulator for applying voltage between the first and second electrodes to bias the deflectable element in one position or to dampen oscillation.

5. The valve of claim 2, wherein the valve further comprises a current regulator for applying an alternating current to at least one of the electrodes.

6. The valve of claim 2, wherein the current regulator is further adapted to adjust at least one of DC voltage, or alternating current amplitude, frequency or phase in response to a control signal.

7. The valve of claim 1, wherein the valve further comprises at least one impedance sensor for monitoring oscillations of the deflectable member.

8. An array of valves, each valve being substantially as described in claim 1, and a controller.

9. A microfluidic valve assembly for controlling the flow of pulsed fluid with a plurality of valves, each valve comprising
   a channel to guide flow of a fluid; and an deflectable valve element disposed and configured to oscillate within the channel, and capable, when activated by a controller, of oscillating in response to fluid pulses to permit fluid passage, and the assembly further comprising electrical controls for activating a subset of the plurality of valves.

10. The valve of claim 9, wherein the assembly further comprises at least one impedance sensor for monitoring movement of the deflectable member.

11. A microfluidic shunt valve for controlling the flow of pulsed fluid comprising a micro-machined structure defining a channel to guide flow of a fluid therethrough in a primary direction;

an deflectable valve element disposed within the channel, and configured to oscillate in an open position in response to fluid pulses to permit fluid passage, and a sensor for measuring impedance of an oscillatory frequency of the deflectable valve element.

12. The valve of claim 11, wherein the deflectable valve element is electrically biased in a normally closed valve position.

13. The valve of claim 11, wherein the valve further comprises a sensor for measuring changes in impedance.

14. The valve of claim 11, wherein the valve further comprises a controller for modulating the oscillatory frequency.

15. The valve of claim 14, wherein the controller includes a regulator adapted to apply a current that alternates at a desired frequency.

16. The valve of claim 15, wherein regulator is adapted to apply a direct current bias.

17. A shunt valve for controlling the flow of pulsed fluid comprising:

a valve body with a distal end and a proximal end;

a valve assembly disposed upon a semiconductor chip and having a plurality of oscillating valve elements, wherein each valve element is configured to oscillate in an open position and permit fluid flow when oscillating in response to fluid pulses, wherein each valve element is electrically isolated from at least a portion of the chip to permit impedance measurements of an oscillatory frequency of the valve element.

18. The array assembly of claim 17, further comprising a sensor for measuring changes in impedance of at least one valve element.

19. The array assembly of claim 17, further comprising a controller for modulating the oscillatory frequency.

20. The array assembly of claim 19, wherein the controller includes a voltage applicator adapted to apply a current that alternates at a desired frequency.

21. The array assembly of claim 20, wherein voltage applicator is adapted to apply a direct current bias.

22. A microfluidic shunt valve for controlling the flow of pulsed fluid comprising a valve body having at least one inlet and at least one outlet and defining a passageway for a pulsed fluid therebetween;

an oscillating valve element configured to oscillate in an open position in response to fluid pressure pulses and thereby permit fluid passage through the valve; and a controller for selectively applying a bias voltage to the oscillating valve element in a closed position to prevent fluid passage.

23. The valve of claim 22, wherein the valve further comprises at least a first electrode and a second electrode, the first electrode associated with the oscillating valve element and isolated from the second electrode such that a bias voltage applied by the controller between the first and second electrodes causes occlusion of the valve.

24. The valve of claim 22, wherein the valve further comprises at least a first electrode and a second electrode, the first electrode associated with the oscillating valve element and a sensor for measuring changes in impedance of a voltage applied across the electrodes.

25. A microfluidic valve assembly for controlling the flow of pulsed fluid, the assembly comprising a plurality of channels to guide flow of a pulsed fluid; and a first deflectable valve element disposed within a first channel and configured to oscillate at a first resonant oscillatory frequency and permit fluid flow when oscillating in the first channel, at least one other deflectable valve element disposed within a second channel and configured to oscillate at a second resonant oscillatory frequency and permit fluid flow when oscillating in the second channel, and electrical controls for activating at least a subset of the plurality of valves.

26. The valve of claim 25, wherein the valve further comprises a sensor for measuring changes in impedance of a voltage applied across electrodes associated with each of the deflectable elements such that a controller can select at least one valve having a resonant frequency that approximates the pulse rate of the fluid.

27. A microfluidic shunt valve for controlling the flow of pulsed fluid comprising a valve body having at least one inlet and at least one outlet and defining a passageway for a pulsed fluid therebetween; and an oscillating valve element configured to oscillate in an open position within the passageway and permit fluid flow when oscillating in response to fluid pressure pulses and having a deflectable element with a resonant frequency that permits fluid passage through the valve.

28. The valve of claim 27 wherein the deflectable element comprises a cantilever element.

29. The valve of claim 27, wherein the valve further comprises at least a first electrode and a second electrode, the first electrode associated with the oscillating valve element and isolated from the second electrode.

30. The valve of claim 29, wherein the valve further comprises a controller for applying a bias voltage applied between the first and second electrodes to cause occlusion of the valve.

31. The valve of claim 29, wherein the valve further comprises a sensor for measuring changes in impedance of a voltage applied across the electrodes.

32. The valve of claim 29, wherein the controller includes a regulator adapted to apply a current that alternates at a desired frequency.

33. The valve of claim 32, wherein the controller further comprises controls for modulating the oscillatory frequency.

* * * * *

UNITED STATES PATENT AND TRADEMARK OFFICE
CERTIFICATE OF CORRECTION

PATENT NO. : 7,618,391 B2
APPLICATION NO. : 11/109987
DATED : November 17, 2009
INVENTOR(S) : Madsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 167 days.

Signed and Sealed this

Twenty-sixth Day of October, 2010

David J. Kappos
*Director of the United States Patent and Trademark Office*